United States Patent
Haubach

[11] Patent Number: 5,925,439
[45] Date of Patent: Jul. 20, 1999

[54] LIQUID-ABSORBENT SANITARY CELLULOSE PRODUCT

[75] Inventor: Klaus Karl Ferdinand Haubach, Ludwigshafen, Germany

[73] Assignee: The Procter & Gamble Company, Cincinnati, Ohio

[21] Appl. No.: 08/913,375

[22] PCT Filed: Mar. 4, 1996

[86] PCT No.: PCT/US96/02923

§ 371 Date: Dec. 17, 1997

§ 102(e) Date: Dec. 17, 1997

[87] PCT Pub. No.: WO96/29967

PCT Pub. Date: Oct. 3, 1997

[30] Foreign Application Priority Data

Mar. 29, 1995 [DE] Germany ................ 295 05 307 U

[51] Int. Cl.[6] ................ B32B 1/00; A61F 13/15
[52] U.S. Cl. .............. 428/178; 428/402; 428/913; 602/56; 602/58; 604/358; 604/364; 604/368; 604/385.1

[58] Field of Search .................. 428/150, 167, 428/172, 402, 143, 168, 178, 913; 602/56, 58, 60; 604/358, 364, 367, 368, 369, 385.1

[56] References Cited

U.S. PATENT DOCUMENTS 4,055,180  10/1977  Karami ........................ 128/287

*Primary Examiner*—Donald Loney
*Attorney, Agent, or Firm*—Theodore P. Cummings; Steven W. Miller; Jacobus C. Rasser

[57] ABSTRACT

A liquid-absorbent sanitary cellulose product, in particular a diaper, sanitary napkin or the like, comprises a liquid-proof back layer (2) and an absorbent body (3). A storage layer (5) is arranged between the absorbent body (3) and the back layer (2), this storage layer (5) consisting of a layer of non-woven material (6) profiled in the direction of thickness (D) of the product by chamber-like impressions (7) being formed, into each of which are inserted super-absorbent hydrogel particles (8).

9 Claims, 2 Drawing Sheets

LIQUID-ABSORBENT SANITARY CELLULOSE PRODUCT

The invention relates to a liquid-absorbent sanitary cellulose product, such as diapers, sanitary napkins or the like, provided with a liquid-proof back layer and an absorbent body. The latter may consist of a pad of cellulose flakes or a so-called air-laid material in usual manner. The latter is used in particular for thin sanitary cellulose products, such as sanitary napkins or panty shields.

Moreover it is known from the prior art to insert so-called superabsorbers into sanitary cellulose products in order to improve their absorptivity and liquid retention capacity. As is generally known, such superabsorbers—i.e. superabsorbent hydrogel particles—are for example blown into the stream of flakes for forming an absorbent body, so that the hydrogel particles are distributed in the volume of the absorbent body.

The insertion and distribution of the hydrogel particles is especially problematic, as an even distribution over the entire base of the cellulose product is not desired. Instead, the majority of the hydrogel particles should be located where the greatest accumulation of liquid is to be expected during use of the cellulose product. Furthermore the use of hydrogel is limited, as too great a concentration of hydrogel particles causes the effect of so-called "gel-blocking", the blocking effect of the swelling particles preventing any further absorption of liquid as well as its transportation to areas of the absorbent body not yet supplied with liquid. Another substantial disadvantage of the conventional insertion of hydrogel particles into sanitary cellulose products consists in that the hydrogel particles can hardly be localized, their migration being undefined during the insertion and thereafter, so that often a disadvantageous distribution of particles is obtained. Thus the hydrogel particles cannot reach their full absorptivity.

Based on mentioned deficiencies it is an object of the invention to improve the structure of sanitary cellulose products of the generic type in such a manner that a defined insertion of hydrogel particles is possible.

This object is achieved by the features of the characterizing part of claim 1. Accordingly a storage layer is arranged between the absorbent body and the back layer, the storage layer consisting of a layer of non-woven material profiled in the direction of thickness of the product by chamber-like impressions being formed, into which are inserted superabsorbent hydrogel particles.

By means of this structure, the super-absorbent hydrogel particles are placed exactly in the desired target areas of the cellulose product and held there. Thus a loss of hydrogel material during production is reduced. Moreover, the storage layer thus obtained enables a reduction of thickness of the absorbent body so that for example a very thin air-laid material can be used. The actual storage of the body liquid takes place in the storage layer itself. Altogether, this favors the construction of thin sanitary cellulose products at a low material consumption.

Additional features, details and advantages of the invention can be taken from the subclaims or the following description, respectively, in which an embodiment of the subject matter of the invention is explained, taken in conjunction with the attached drawing, in which

Figure 1:
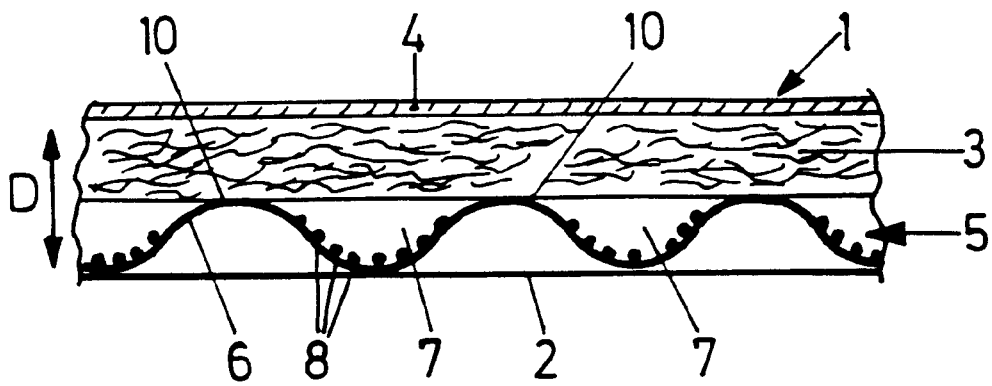
FIG. 1 shows a partial vertical section through a diaper.

As can be seen from FIG. 1, a diaper designated in its entirety by 1 comprises a liquid-proof back layer 2 consisting of a thin polyethylene film, an absorbent body 3 formed of cellulose flakes or air-laid material, and a core layer 4 consisting of a non-woven material.

Figure 2:
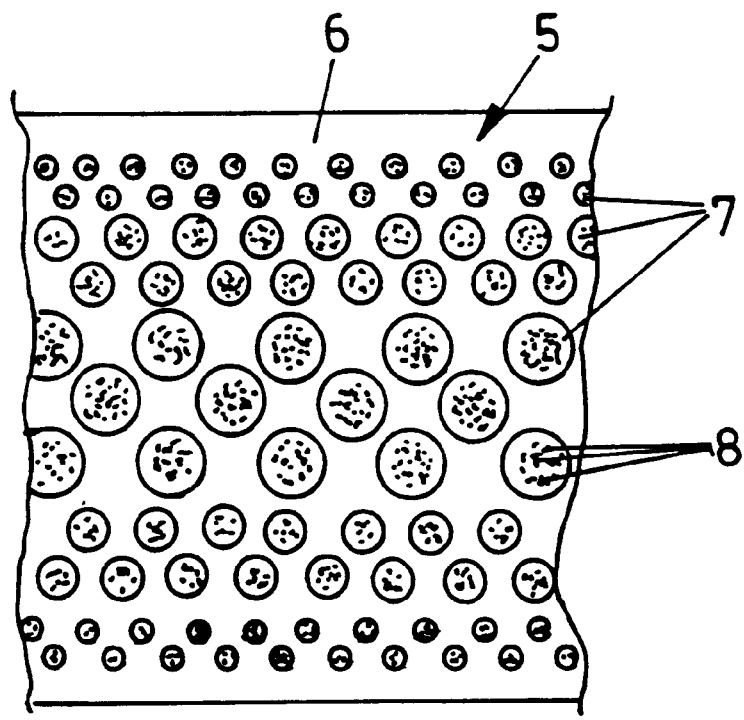
FIG. 2 shows a plan view of the non-woven layer forming the storage layer.

Between the back layer 2 and the absorbent body 3, a storage layer 5 is arranged, consisting of a non-woven layer 6 profiled in the direction of thickness D of the diaper 1. By means of this profiling, chamber-like impressions 7 are formed in the non-woven layer 6, which impressions are in the shape of calottes when viewed from above (FIG. 2). Super-absorbent hydrogel particles 8 are applied to the inside, facing upwards, of the impressions 7 in a manner which still remains to be specified.

By means of the above-mentioned structure of the storage layer 5, the hydrogel particles 8 are virtually inserted into defined chambers formed by the impressions 7. The combined chamber volume of all impressions in the diaper 1 is designed such that it can take up at least a desired quantity of liquid that may occur. Moreover, the individual chamber-like impressions 7 in the storage layer 5 may vary in volume, depending on the quantity of liquid expected to occur in a certain area of the diaper. For example, the impressions 7 arranged in the gusset area of the diaper 1 have a greater volume than those in the front, rear and lateral portions.

The amount of hydrogel particles 8 inserted into the individual impressions 7 is to be designed advantageously such that the hydrogel particles, after the absorption of body liquid, fill out the impressions 7 without the occurence of gel-blocking. Accordingly, smaller impressions 7 in areas of lower liquid accumulation will be provided with a smaller amount of hydrogel particles 8.

In order to guarantee a secure insertion of hydrogel particles 8 into the impressions 7, a covering layer 9 is applied to the non-woven layer 6, which covering layer 9 may be a separate non-woven layer or the absorbent body 3 itself in the form of a relatively firm air-laid material. The separate covering layer 9 can be seen in FIG. 3. For joining the non-woven layer 6 to the covering layer 9, a glued joint 10 is applied, surrounding the impression 7. Thus, the non-woven layer 6 and the covering layer 9 form a kind of laminate. The junction can also be done mechanically, e.g. by pressing the non-woven layer 6 and the covering layer 9. Thus the penetration of liquid through the entire structure and thus the absorptivity is not as much reduced as with the above-mentioned glued joint 10.

Figure 3:
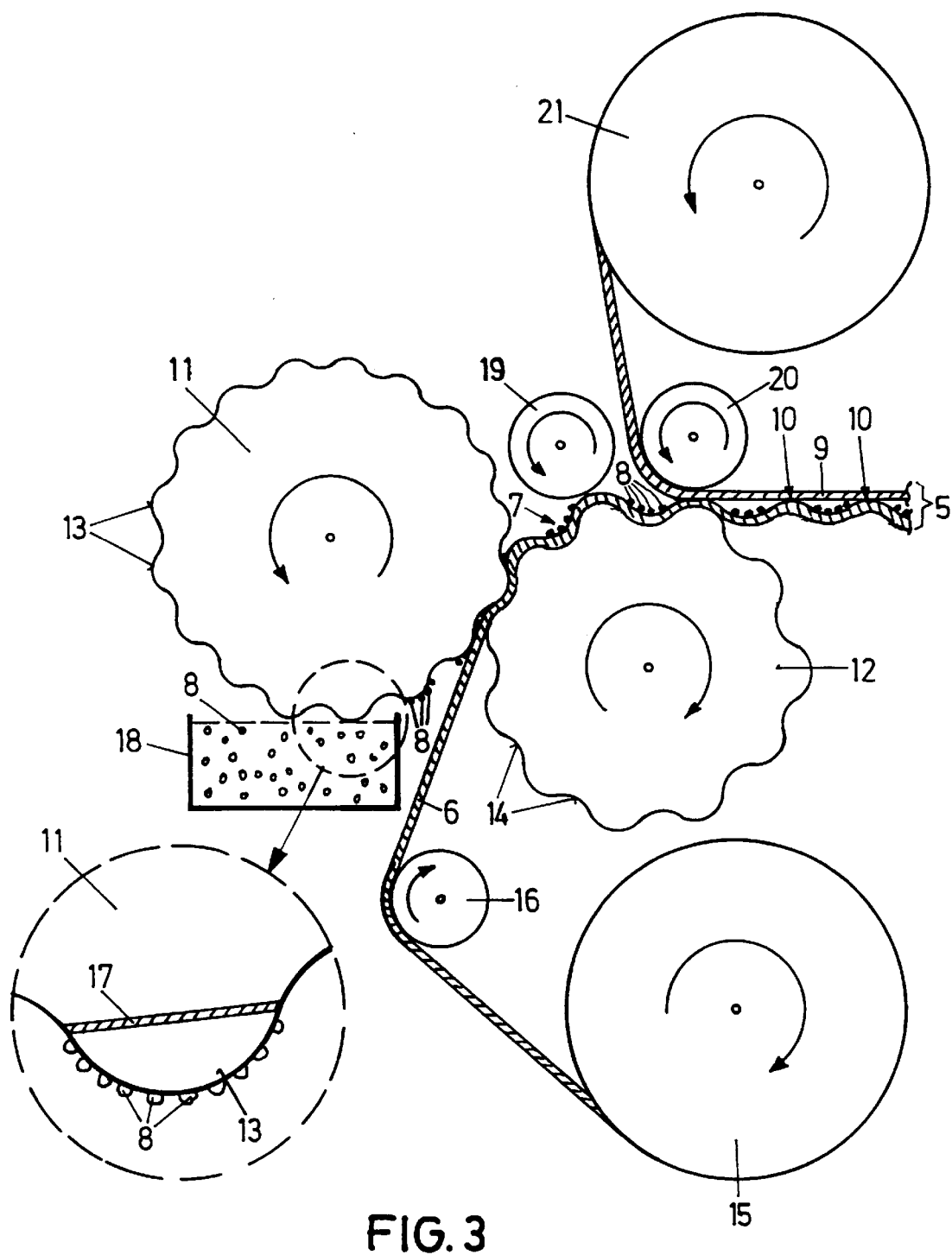
FIG. 3 shows a schematic view of a production arrangement for the storage layer with a back layer.

FIG. 3 shows a production arrangement for the storage layer 5. The core of the arrangement is a pair of embossing rolls, consisting of a top roll 11 and a bottom roll 12. The top roll 11 comprises embossing heads 13 in the form of spherical segments, whereas the bottom roll 12 is provided with corresponding calotte-type impressions 14. The non-woven layer 6 held on a supply roll 15 runs via a deflection pully 16 and continues through the gap between the top roll 11 and the bottom roll 12. By means of the embossing heads 13 of the top roll 11 engaging with the impressions 14 of the bottom roll 12, the impressions 7 are embossed into the non-woven layer 6.

The top roll 11 at the same time serves as a transfer roll for the insertion of the hydrogel particles 8 into the impressions 7. For this purpose—as can be seen from the enlarged detail in FIG. 3—the embossing heads 13 can be electrostatically charged and are electrically insulated from the roll body by means of an insulating layer 17. During rotation of the top roll 11, the electrostatically charged embossing heads dive into a reservoir 18 filled with hydrogel particles 8. Depending on the electrostatic charge, a defined amount of hydrogel particles 8 is picked up during the immersion and, in the gap between the rolls, is transferred to the non-woven layer 6 into the impressions 7 simultaneously embossed.

Downstream of the pair of rolls 11, 12 a glue spreading roll 19 is arranged, spreading glue on the raised areas surrounding the impressions 7, for the production of glued joints 10. Downstream thereof a pressing roll 20 is arranged, which, as the glue spreading roll 19, cooperates with the bottom roll 12. The covering layer 9, after being drawn off the supply roll 15, is supplied via the pressing roll 20 and is thus glued together with the non-woven layer 6. In order to keep the non-woven layer 6 in contact with the bottom roll 12 during its travel on the latter, the non-woven layer 6 is fixed by vacuum actuation.

Summing up, the present invention has the following advantages:

- Contrary to the prior art, where only horizontally delimited chambers are used, for the subject matter of the invention additional chambers, extending vertically—i.e. in the direction of thickness of the cellulose product—are produced in the form of the impressions 7.
- Thus the effectiveness of the absorbent materials is improved, as they are positioned exactly and fixed in their position in the product in order to achieve optimal characteristics of the product. In particular, the superabsorbent hydrogel particles 8 cannot migrate to areas, where they cannot be used to full capacity.
- The construction allows a higher pressing of the cellulose product and thus a reduction of the packing volume.
- The thickness of the absorbent body can be reduced, so that thinner sanitary products can be produced.
- The production losses, as they occur e.g. in the charging with hydrogel particles of the stream of flakes forming an absorbent body, are avoided.

I claim:

1. A liquid-absorbent sanitary cellulose product having a direction of thickness, comprising a liquid-proof back layer and an absorbent body, wherein a storage layer is arranged between the absorbent body and the back layer, the storage layer consisting of a layer of non-woven material profiled in the direction of thickness of the product by chamber shaped impressions being formed, the chamber shaped impressions being positioned subjacent to the absorbent body and above the liquid-proof back layer, the chamber shaped impressions further comprising superabsorbent hydrogel particles and surface areas surrounding the chamber shaped impressions.

2. A cellulose product according to claim 1, wherein the chamber shaped impressions are in the shape of calottes.

3. A cellulose product according to claim 1 or claim 2, wherein the volume of the chamber shaped impressions varies in relation to the surface of the cellulose product and depends on the local occurrence of liquid.

4. A cellulose product according to claim 1, wherein the surface areas, surrounding the impressions of the non-woven layer are connected with a covering layer (9).

5. A cellulose product according to claim 4, wherein the covering layer is formed by the absorbent body.

6. A cellulose product according to claim 4, wherein the covering layer is glued together with the layer of non-woven material.

7. A cellulose product according to claim 4, wherein the covering layer is mechanically connected with the layer of non-woven material.

8. A cellulose product according to claim 1, wherein the hydrogel particles are inserted during the embossing of the layer of non-woven material into the impressions by means of an embossing roll with electrostatically charged embossing heads which pick up the hydrogel particles from a reservoir.

9. A cellulose product according to claim 3 wherein the volume of the super-absorbent hydrogel particles varies in relation to the surface of the cellulose product and the local occurrence of liquid.

* * * * *